United States Patent
Letourneur et al.

(10) Patent No.: US 8,329,955 B2
(45) Date of Patent: Dec. 11, 2012

(54) CONTINUOUS PREPARATION OF AMINES BY NITRILE COMPOUND HYDROGENATION

(75) Inventors: Didier Letourneur, Rixheim (FR); Philippe Leconte, Ribeauvillé (FR); Jean-Francis Spindler, Ternay (FR); Patrick Lermusiaux, Lyons (FR); Vincent Boschat, Cusset (FR)

(73) Assignee: Rhodia Operations, Aubervilliers (FR)

( * ) Notice: Subject to any disclaimer, the term of this patent is extended or adjusted under 35 U.S.C. 154(b) by 289 days.

(21) Appl. No.: 12/681,397

(22) PCT Filed: Oct. 2, 2008

(86) PCT No.: PCT/EP2008/063233
§ 371 (c)(1),
(2), (4) Date: May 26, 2010

(87) PCT Pub. No.: WO2009/043906
PCT Pub. Date: Apr. 9, 2009

(65) Prior Publication Data
US 2010/0267989 A1    Oct. 21, 2010

(30) Foreign Application Priority Data
Oct. 4, 2007 (FR) ..................... 07 06966

(51) Int. Cl.
*C07C 209/48*    (2006.01)
(52) U.S. Cl. .................. 564/492; 564/490; 564/491
(58) Field of Classification Search .................. None
See application file for complete search history.

(56) References Cited

U.S. PATENT DOCUMENTS

| | | | | |
|---|---|---|---|---|
| 5,869,653 | A | * | 2/1999 | Johnson ............ 540/531 |
| 5,981,790 | A | * | 11/1999 | Cotting et al. ........ 558/459 |
| 6,232,488 | B1 | | 5/2001 | Boschat et al. |
| 6,518,449 | B1 | | 2/2003 | Boschat et al. |
| 6,521,779 | B1 | * | 2/2003 | Boschat et al. ........ 558/459 |

FOREIGN PATENT DOCUMENTS

| | | |
|---|---|---|
| FR | 2773086 A1 | 7/1999 |
| WO | WO 99/26917 A1 | 6/1999 |

OTHER PUBLICATIONS

International Search Report corresponding to PCT/EP 2008/063233 mailed on Jan. 22, 2009.

* cited by examiner

*Primary Examiner* — Brian J Davis
(74) *Attorney, Agent, or Firm* — SNR Denton US LLP

(57) ABSTRACT

Amino compounds are continuously prepared by hydrogenation of nitrile compounds in the presence of a catalyst, and more particularly diamines are prepared by the continuous hydrogenation of dinitrile compounds in the presence of a Raney metal catalyst and in the absence of an alcoholic solvent; the subject process includes extracting a portion of the catalyst present in the reaction medium, the extracted portion of the catalyst is submitted to a regeneration for providing a catalyst having a catalytic activity lower than that of a fresh catalyst but still high and the regenerated catalyst is recycled to the reaction medium together with fresh catalyst according to a predetermined ratio, whereby the consumption of catalyst is reduced per ton of amines produced.

27 Claims, 2 Drawing Sheets

CONTINUOUS PREPARATION OF AMINES BY NITRILE COMPOUND HYDROGENATION

CROSS-REFERENCE TO PRIOR APPLICATIONS

This application claims is a national stage of PCT/EP 2008/063233, filed Oct. 2, 2008, and designating the United States (published in the French language on Apr. 9, 2009 as WO 2009/043906 A1; the title and abstract were also published in English), which claims priority to FR 0706966, filed Oct. 4, 2007, each hereby expressly incorporated by reference in its entirety and each assigned to the assignee hereof.

The present invention relates to a process for the manufacture of amine compounds by hydrogenation of nitrile compounds in the presence of a catalyst.

It relates more particularly to a process for the manufacture of diamines by continuous hydrogenation of dinitrile compounds in the presence of a catalyst based on a Raney metal and in the absence of alcoholic solvent.

One of the processes for the manufacture of amine compounds used industrially is the catalytic hydrogenation of nitrile compounds.

Thus, hexamethylenediamine, which is an important chemical intermediate in the manufacture of numerous compounds or polymers, is produced predominantly by catalytic hydrogenation of adiponitrile.

Mention may be made, by way of example, of the processes for the hydrogenation of adiponitrile in the presence of a metal oxide as catalyst, such as iron oxide or cobalt oxide. These processes are generally carried out at high pressures and temperatures and often in the presence of ammonia.

Other hydrogenation processes which are widely operated consist in using, as catalyst, a system based on a Raney metal, more particularly Raney nickel or Raney cobalt, in the presence of alcohol, or of water and of a basic compound as cocatalyst. In these processes, the reaction is carried out at relatively low pressures and temperatures and in the absence of ammonia. The latter hydrogenation processes with a catalyst based on a Raney metal can be employed in certain types of reactor. This is because, as the catalyst is pyrophoric, the reactors used have to make possible efficient control of the continuous introduction of the catalyst into the reaction medium. It is also necessary to control the amount of catalyst suspended in the reaction medium and to provide managed and controlled circulation of this suspension.

However, the activity of these catalysts can be greatly affected when they are used under certain conditions in processes for the hydrogenation of nitrile compounds.

A paper published in Chemical Engineering Science, Vol. 47, No. 9-11, 2 289 94 (1992), indicates that nitrile compounds deactivate catalysts based on Raney nickel or Raney cobalt. In order to reduce this deactivation, the proposal was made, in the paper published in Chemical Engineering Science, Vol. 35, 135-141 (1980), to use a reactor with a high rate of circulation of the reaction medium in order to obtain optimum mixing conditions and a turbulent flow in order to prevent the formation of regions exhibiting a high concentration of nitrile compounds. This is because a high concentration of nitrile compounds results in deactivation of the catalyst.

All these processes use, as solution for reducing the decline in the activity of the catalyst, systems which make it possible to have efficient mixing of the reaction medium and thus to have a concentration of reactants and catalysts which are identical at any point in the reactor.

Such a quality of mixing is difficult to obtain and requires complex devices, such as those described in Patent Application WO 00/37424, which relates to the use of static mixers for improving the quality of the mixing and the homogeneity of the concentrations at any point in the reactor.

In addition, these solutions can be applied when the hydrogenation reaction is carried out continuously in a reactor operating under plug-flow conditions, such as bubble columns operating with circulation of a bed of catalyst in suspension, reactors comprising a bubble column and a cyclone head for separating the gases, referred to hereinafter as reactors of RTC type.

Another characteristic of these processes lies in the phenomenon of rapid deactivation of the catalyst by formation and deposition of aluminate on the catalyst.

In order to prevent this problem or to reduce it, the proposal have been made to add an alcohol to the reaction medium in order to make it possible to dissolve the aluminate and to reduce its deposition on the catalyst. However, it was necessary to carry out periodic shutdowns of the plant in order to clean and remove the deposits of aluminates on the parts of the equipment due to crystallization of the aluminate.

This process also has the disadvantage of comprising distillation and alcohol-separation operations. In addition, the alcohol could react with the amine formed, such as hexamethylenediamine (HMD), to form an impurity, such as the imine of N-ethyl/HMD, which is difficult to separate form the diamine formed. Hydrogenation processes which are free of alcohol but with water have also been proposed, such as described in U.S. Pat. Nos. 3,056,837, 4,429,159 and 4 491 673, for example.

However, in order to maintain a high activity of the catalyst in the reaction medium, it was necessary to withdraw a significant amount of spent catalyst and to replace this amount of catalyst with fresh catalyst. The catalyst consumption was thus high and affected the economics of the process.

One of the aims of the present invention is to provide a continuous process for the hydrogenation of nitrile compounds to give amine compounds in the presence of a catalyst based on Raney metal in a medium comprising water, in the absence of alcohol, which makes it possible to maintain a suitable catalytic activity in the reactor with a low consumption of catalyst per tonne of amine compound produced.

To this end, the invention provides a process for the manufacture of compounds comprising at least one amine functional group by hydrogenation of a compound comprising at least one nitrile functional group which consists in:

feeding a gas comprising hydrogen and a component comprising at least one nitrile functional group to a reactor of plug-flow type in which a reaction medium circulates, the reaction medium comprising suspended particles of catalyst based on Raney metal, an inorganic base and water, withdrawing, at the outlet of the plug-flow reactor, a portion of the reaction medium comprising the compound comprising at least one amine functional group, after separating the catalyst, and recycling the other portion to the plug-flow reactor, recycling the separated catalyst to the plug-flow reactor, feeding a stream of fresh catalyst to the plug-flow reactor, characterized in that a portion of the separated catalyst is subjected to a regeneration process before being recycled to the reaction medium, the said regeneration process comprising a stage of washing the catalyst with water in order to remove most of the organic compounds, the washed catalyst being subjected to treatment with a base in order to dissolve most of the aluminates formed, followed by washing with an aqueous alkali metal hydroxide solution and/or water.

The term "fresh catalyst" is understood to mean a catalyst which has not been used in a hydrogenation reaction.

According to one characteristic of the invention, the flow rate by weight R of recycled regenerated catalyst and the flow rate by weight N of fresh catalyst supplied should advantageously satisfy the following equation I:

$$0.60 \leq \frac{R}{R+N} \leq 0.95 \quad (I)$$

Preferably, these flow rates R and N should advantageously satisfy the following equation II:

$$0.70 \leq \frac{R}{R+N} \leq 0.90 \quad (II)$$

This control of the flow rates, R and N, of regenerated catalyst and fresh catalyst makes it possible to control the mean activity of a catalyst in the reaction medium and thus to optimize the flow rate of fresh catalyst in order to minimize the consumption of catalyst per tonne of amine produced while maintaining optimum conditions for operation of the process, for example degree of conversion of the nitrile or selectivity for diamine.

The mass flow rates R and N are expressed as weight of catalyst per unit of time.

The mean flow rate by weight of fresh catalyst N is determined by the productive output desired for the plant or the hydrogenation process and depends more particularly on the flow rate of nitrile compounds fed to the plant.

The catalysts suitable for the invention are Raney metals, such as Raney nickel or Raney cobalt, preferably Raney nickel.

Promoter elements can advantageously be used with the Raney metal. These promoter elements are chosen from the elements belonging to Groups IIB, and IVB to VIIB of the Period Table of the Elements. Advantageously, the promoter elements are chosen from the group consisting of titanium, chromium, zirconium, vanadium, molybdenum, manganese, cobalt, nickel, zinc, iron and their combinations.

According to the process of the invention, the portion of catalyst separated from the reaction medium is subjected to a regeneration process which makes it possible to obtain a catalytic activity corresponding to 35% to 80%, preferably 40% to 70%, of the catalytic activity of the fresh catalyst.

This activity of the catalyst is expressed by the molar amount of hydrogen consumed during the reduction of the adiponitrile to give hexamethylenediamine for a defined amount of Raney nickel catalyst per unit of time under conditions of temperature and pressure and a KOH/weight of catalyst ratio which are determined for the measurement method.

The initial activity of the catalyst is determined by carrying out the procedure described below:

50 ml of demineralized water deaerated with argon are poured into a 250 ml beaker.

Approximately 2 grams of slurry formed of catalyst to be analysed are withdrawn using a spatula.

The test sample is introduced into the beaker and approximately 100 ml of demineralized and deaerated water are added.

The medium is stirred in order to suspend the catalyst to be analysed.

The water is separated from the catalyst by placing a magnetic plate at the bottom of the beaker.

The demineralized and deaerated water is drained.

150 ml of demineralized and deaerated water are poured into the beaker.

The beaker placed on the magnet: the aqueous washing liquor is drained and then 50 to 100 ml of demineralized and deaerated water are added.

The catalyst is washed with demineralized and deaerated water. At the end of the washing operations, the pH of the water must be in the vicinity of 7.

A pycnometer is filled with the supernatant liquid of the catalyst.

The pycnometer is weighed in order to define the zero of the balance.

The pycnometer is removed from the balance.

A small amount of water is removed from the pycnometer with a pipette.

The catalyst is withdrawn from the beaker with the same pipette.

An amount of catalyst is introduced into the pycnometer and the pycnometer is readjusted with the supernatant liquid.

The pycnometer is weighed and the difference in weight (W) between the pycnometer filled with water plus the catalyst and the pycnometer filled with water is read.

The weight of catalyst $w_{catalyst}$ is equal to $1.15 \times W$.

The amount of catalyst in the pycnometer is readjusted by repeating the above weighing operations until the desired amount is obtained:

The amount of catalyst to be withdrawn is advantageously equal to:

Approximately 0.4000 g precisely of spent, regenerated or fresh washed catalyst:

(0.3960 g $\leq w_{catalyst} \leq$ 0.4040 g)

The weight $w_{catalyst}$ of catalyst introduced into the pycnometer is recorded (accuracy: 0.0001 gram).

The clean and dry reactor and its support are placed on the tare balance. The balance is zeroed.

The contents of the pycnometer are decanted into a clean and dry reactor.

The pycnometer is rinsed with the necessary amount of demineralized water to collect all of the catalyst introduced into the pycnometer.

As much as possible of water is removed using the magnetic plate on the bottom of the reactor.

6.8N potassium hydroxide KOH is added to the catalyst using the suitable microsyringe, i.e. 47 µl.

The solution is made up with demineralized water in order to obtain a weight of solution in the reactor equal to 4.66 g.

37.8 g of pure HMD are added to the reactor.

The reactor is inserted into the pilot-scale device and heating is begun (set temperature at 80° C.).

The headspace of the reactor is purged 3 times with nitrogen.

The hydrogen supply is placed at a pressure of 50 bar.

The headspace of the reactor is purged with hydrogen by admission of hydrogen and discharge. The operation is repeated 3 times while maintaining or reestablishing the pressure in the hydrogen supply.

At the end of the three purges of the reactor with hydrogen, the reactor is pressurized to 20 bar of hydrogen.

Stirring is begun (set temperature of 80° C. and stirring rate of 2000 rev/min).

Approximately 6.00 grams precisely of adiponitrile are withdrawn with a glass syringe equipped with its extended needle.

The balance is zeroed with the charged syringe equipped with its needle.

The adiponitrile is introduced into a dropping funnel.

The empty syringe equipped with its needle is weighed.

The weight of adiponitrile $w_{ADN}$ introduced into the dropping funnel is recorded (it must be between 5.70 and 6.30 grams).

The reactor is placed under hydrogen pressure from the hydrogen supply and a pressure of 50 bar is reestablished in the supply. It is confirmed that the supply and reactor pressures remain constant.

Once the temperature and the stirring have been reached, the valve of the dropping funnel is opened, first slightly and then completely in a single operation, in order to introduce the AdN into the reactor.

The pressure inside the reactor should rise to 25 bar.

The feed of hydrogen to the reactor from the supply is kept open until the hydrogen pressure curve is stable.

Throughout the duration of the reaction, the hydrogen pressure in the supply is recorded as a function of the time.

When the hydrogen pressure in the reactor is stable, the hydrogen feed to the reactor is closed.

Heating of the reactor is halted and the reaction medium is cooled to a temperature of 45° C.

The reactor is slowly decompressed and stirring is halted.

The headspace of the reactor is purged three times with nitrogen.

The contents of the reactor are drained into a container with rinsing with demineralized water.

The activity of the catalyst is determined by the initial rate of the reaction, given by the following formula:

$$R_{initial} = \frac{4 \times w_{ADN}}{108 \times w_{catalyst} \times 60 \times \Delta t_{initial}}$$

$\Delta t_{initial}$ is the time in minutes which the hydrogenation would take if the catalyst were continually replaced during the reaction. It is determined by the abscissa of the point of intersection between the slope of the curve for recording the pressure at the start of the reaction and the slope at the end of the reaction, which is generally zero. This curve represents the variation in the hydrogen pressure in the supply as a function of the time.

The initial rate of hydrogenation is expressed in moles of $H_2$/g of cata/s.

According to the invention, the regeneration process comprises a first stage of washing the catalyst to be regenerated in order to remove most of the organic compounds, in particular amine formed, such as hexamethylenediamine, for example.

This washing is carried out with water, several successive washing operations advantageously being carried out in order to obtain, in the final aqueous washing liquor, a concentration by weight of organic compounds of less than or equal to 1% by weight. Preferably, this concentration of organic compounds is measured by determination of the amount of amine present in the aqueous washing liquor.

This washing can also be carried out continuously in one or more countercurrent flow columns or in a column comprising the catalyst to be washed in the form of a fixed bed.

Advantageously, the washing is carried out with water at a temperature of between 10° C. and 50° C., preferably with water at ambient temperature (20-25° C.), in order to prevent fouling of the columns or washers.

The washed catalyst is subsequently subjected to treatment with a strong base in order in particular to dissolve the aluminates formed. Use may preferably be made, as suitable base, of alkali metal hydroxides, sodium hydroxide being the preferred hydroxide.

The base solution used comprises from 10% to 25% by weight of sodium hydroxide.

The treatment is preferably carried out at a temperature of greater than 80° C. and advantageously at the boiling point of the sodium hydroxide solution.

It can be carried out in a batchwise process or in a continuous process.

The duration of treatment with the sodium hydroxide must be sufficient to make possible a regeneration in the catalytic activity corresponding to at least 35% of the catalytic activity of a fresh catalyst, advantageously at least 39%.

In addition, the treatment with a basic compound makes it possible to produce hydrogen by attack on aluminium metal. This hydrogen makes it possible to condition the catalyst.

The catalyst thus treated is subjected to a further washing stage in order to remove the soluble aluminates.

This washing can comprise several successive washing operations or can be carried out continuously in a countercurrent washing column, for example.

The washing is advantageously carried out with water at a temperature of between 40° C. and 90° C. in order to promote the removal of the aluminates. It is also possible to use, as washing liquid, an aqueous alkali metal hydroxide solution, preferably an aqueous sodium hydroxide solution, at a minimum concentration of 0.012 g/l sodium hydroxide, advantageously of between 0.012% by weight and 0.040% by weight. This washing solution can advantageously be used to carry out the final washing stages or throughout the washing process. Washing is carried out until a concentration by weight of alkali metal hydroxide (sodium hydroxide) of greater than or equal to 0.012% by weight is obtained in the final aqueous wash liquor. If the concentration of alkali metal hydroxide (sodium hydroxide) is less than this value, a risk exists of precipitation of the aluminates.

After washing, the regenerated catalyst is recycled directly to the reaction medium or mixed with the fresh catalyst before feeding to the reaction medium.

The regeneration process is advantageously carried out under air.

However, it is also possible to carry it out under an inert atmosphere or an atmosphere not comprising oxygen.

It is also advantageous to use, as aqueous washing liquors and as sodium hydroxide solution, deoxygenated aqueous liquors and deoxygenated solutions.

The process of the invention applies to the hydrogenation of nitriles or dinitriles to give amines or diamines. It applies in particular to the manufacture of diamines chosen from the group consisting of propylenediamine, diaminobutane, pentamethylenediamine, 2-methylpentamethylenediamine and hexamethylenediamine. It applies more particularly to the hydrogenation of adiponitrile to give hexamethylenediamine.

According to the invention, the hydrogenation reaction is carried out in the presence of a solvent advantageously composed of the amine obtained by the hydrogenation. Thus, in the case of the hydrogenation of adiponitrile, hexamethylenediamine is advantageously used as main component of the reaction medium. The concentration of amine in the reaction medium is advantageously between 50% and 99% by weight, preferably between 60 and 99% by weight, of the liquid phase of the hydrogenation reaction medium.

The hydrogenation reaction is carried out in the presence of water as other component of the reaction medium. This water is generally present in an amount of less than or equal to 50% by weight, advantageously of less than or equal to 20% by weight, in the liquid phase of the total reaction medium and more preferably still between 0.1% and 15% by weight.

The hydrogenation reaction is carried out in the presence of a basic compound, preferably an inorganic base, such as LiOH, NaOH, KOH, RbOH, CsOH and their mixtures. NaOH and KOH are preferably used.

The amount of base added is determined in order to have at least 0.1 mol of base per kilogram of catalyst, preferably between 0.1 and 2 mol of base per kg of catalyst and more advantageously still between 0.3 and 1.5 mol of base per kg of catalyst.

The hydrogenation reaction is carried out at a temperature of less than or equal to 150° C., preferably of less than or equal to 120° C. and more preferably still of less than or equal to 100° C. The reaction temperature is generally between 50° C. and 100° C.

The hydrogen pressure in the reactor is between 0.10 and 10 MPa approximately.

According to a preferred embodiment of the invention, the hydrogenation reaction of the invention is carried out continuously in an apparatus or device described below with reference to the appended FIGS. 1 and 2, which represent block diagrams of an embodiment of an apparatus suitable for the implementation of the invention.

The apparatus suitable for the implementation of the process of the invention makes it possible to produce excellent gas/liquid contact, rapid and efficient separation of these two phases after contact, continuous separation of the hydrogenate and of the catalyst and the recycling of the latter, in a time compatible with the least possible deactivation of the said catalyst.

The said apparatus comprises three main sections: a plug-flow reaction section operating according to the principle of the bubble column with circulation of a suspended catalyst bed, a gas/liquid separation section and a catalyst/liquid separation section with recycling of the said catalyst and withdrawing of the liquid (hydrogenate).

Thus, the apparatus which makes it possible to implement the process comprises, at the plug-flow reactor outlet, a region for decantation of the catalyst particles (the catalyst/liquid separation section), the supernatant phase being recycled to the plug-flow reactor via a first external loop comprising a withdrawal of the medium comprising the amine, the decanted phase being recycled to the plug-flow reactor via a second external loop.

The reaction section generally comprises one or more U-shaped pipes, the branches of which are vertical or slightly inclined with respect to the vertical, one of the branches of each U providing the ascent of the gas/liquid/solid catalyst dispersion and the other the return of the at least partially degassed liquid. It also comprises inlets at the base of the ascending branch: the hydrogen inlet, the dinitrile inlet, the cocatalyst inlet, the catalyst inlet and the recycled catalyst inlet; the catalyst inlet can comprise a single feed for introducing the mixture of fresh catalyst and of regenerated catalyst or two separate feeds for fresh catalyst and for regenerated catalyst. The gas/liquid separation section is composed of a vertical cylinder comprising one or more tangential inlets (coming from the ascending branch of the reactor), one or more tangential outlets (towards the descending branch of the reactor), a gas outlet and an outlet for the reaction mixture towards the liquid/solid separation. The inlet for the gas/liquid/solid catalyst dispersion is inserted at a point situated above the point of departure of the degassed liquid. This part forms a cyclone head.

The liquid/solid separation section is composed of a decanter which makes it possible to separate the hydrogenate from the catalyst and to recycle the said catalyst. The hydrogenate is withdrawn continuously, whereas the catalyst suspension separated in the decanter is brought back to the reaction section upstream of the point of introduction of the hydrogen. A portion of this catalyst suspension is withdrawn in order to be subjected to a regeneration treatment, in accordance with the invention.

Figure 1:
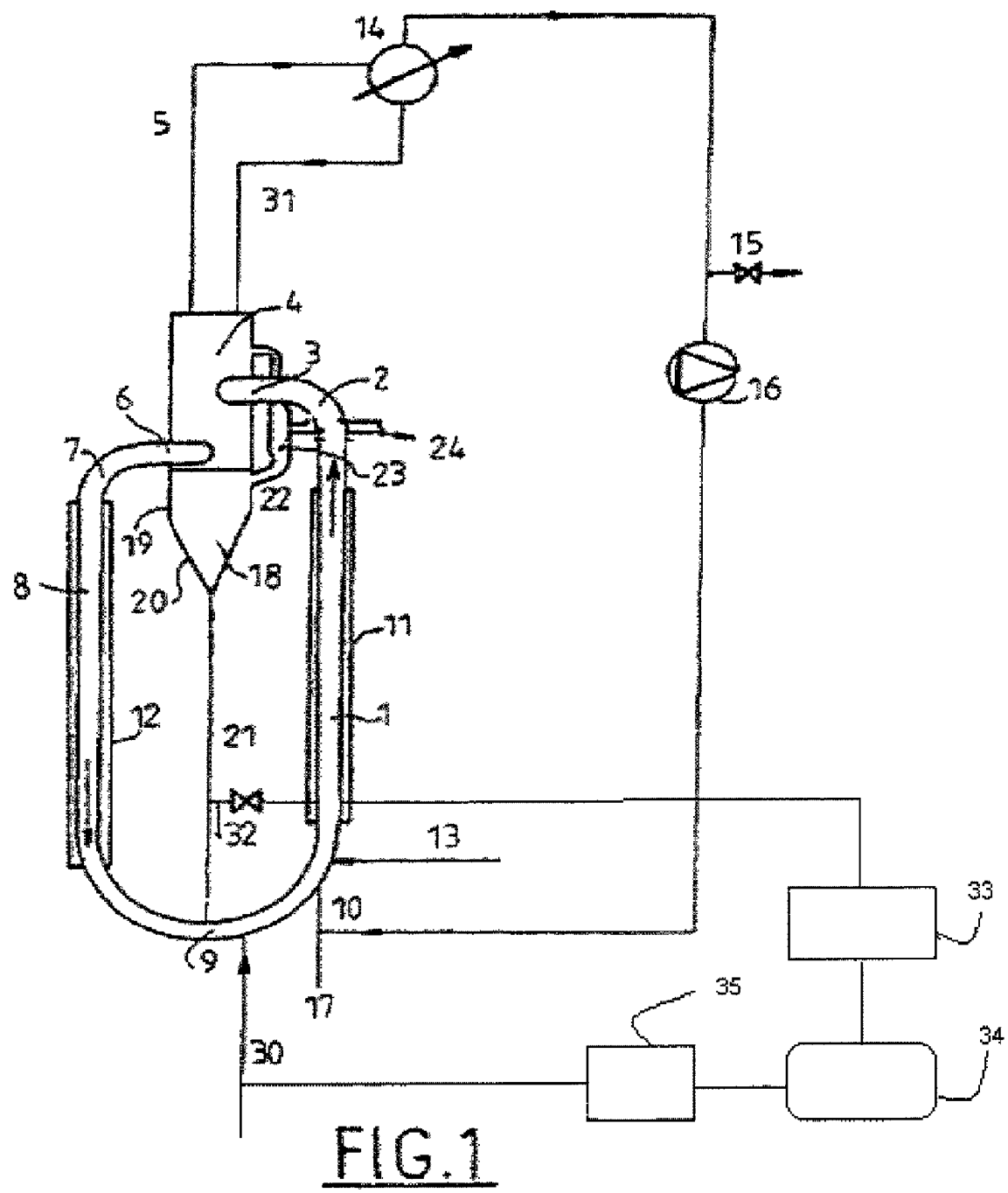
FIG. 1 is an illustration of a apparatus suitable for use in the process described herein.

The apparatus suitable for the process of the invention can be illustrated by way of example by FIG. 1. It comprises a vertical cylindrical pipe (1) connected by an elbowed pipe (2) to a horizontal pipe (3) emerging tangentially in a gas/liquid separator (4) composed of a vertical cylinder with a diameter greater than that of the pipe (1).

The separator (4) comprises a line (5) for discharge of gas or of vapours. A horizontal pipe (6) originating tangentially to the separator and at a point situated below the inlet point of the pipe (3) is connected via an elbowed pipe (7) to a second vertical pipe (8) communicating with the pipe (1) via an elbow (9). The combination of the pipes (1) and (8) and of the elbow (9) forms a U. The pipe (1) comprises, at its base, a line (10) for introducing hydrogen and a line (13) for introducing the dinitrile. The pipes (1) and (8) can comprise, as represented in FIG. 1, a jacket (11) and (12) allowing the circulation of a cooling or heating fluid. The elbow (9) comprises an inlet (30) for catalyst and an inlet (21) for recycled catalyst.

The pipes (1) and (8) can be vertical or slightly oblique (in the latter case, preferably so that their axes converge downwards).

The radii of curvature of the elbows (2, 7, 9) are calculated according to the usual rules of chemical engineering so that the pressure drop in the body circulating throughout the circuit is as low as possible. Their angle of curvature can vary from 45° to 135° and preferably from 60° to 120°.

In FIG. 1, the hydrogen is introduced via a line (10). This line can be equipped with any standard dispersing device but a simple pipe flush with the wall, positioned in the axis of the pipe (1), is sufficient. This line (10) is connected to a hydrogen source and the hydrogen can be introduced at atmospheric pressure or at a higher pressure.

The line (5) for discharge of the gases can be connected to any device for the treatment of the gases separated from the hydrogenate. FIG. 1 illustrates a device according to which the gases resulting from (5) pass into a condenser (14) in which the vapours entrained in the separator (4) are separated from the hydrogen. The condensate obtained is recycled to the apparatus via a line (31). The excess hydrogen subsequently passes into a compressor (16) via a pipeline comprising a bleed system (15) and then it is recycled in (10) after introduction, in (17), of an amount of hydrogen intended to compensate for the hydrogen consumed during the hydrogenation and that which has been bled off.

It is necessary to withdraw the hydrogenate formed degassed and freed from the catalyst. In order to be able to withdraw a clear hydrogenate, that is to say comprising virtually no catalyst, a decanter (18) is placed directly under the separator (4). The liquid/catalyst suspension, the gas phase of which has been separated in the separator (4), enters the decanter (18).

The decanter (18) is composed of a cylinder (19) terminated by a cone (20).

A pipeline (21) serves to continuously return the concentrated catalyst slurry to the elbow (9). The hydrogenate, freed from the catalyst, exits via a pipeline (22) connected to a trap (23) equipped with an overflow (24) which makes it possible to continuously withdraw the clear hydrogenate, the level in the whole of the apparatus being kept constant by the continuous introduction of an equivalent volume of dinitrile, solvent and catalyst mixture. The catalyst decanted in the cone (20) is recycled to the pipe (9) via the line (21).

Figure 2:
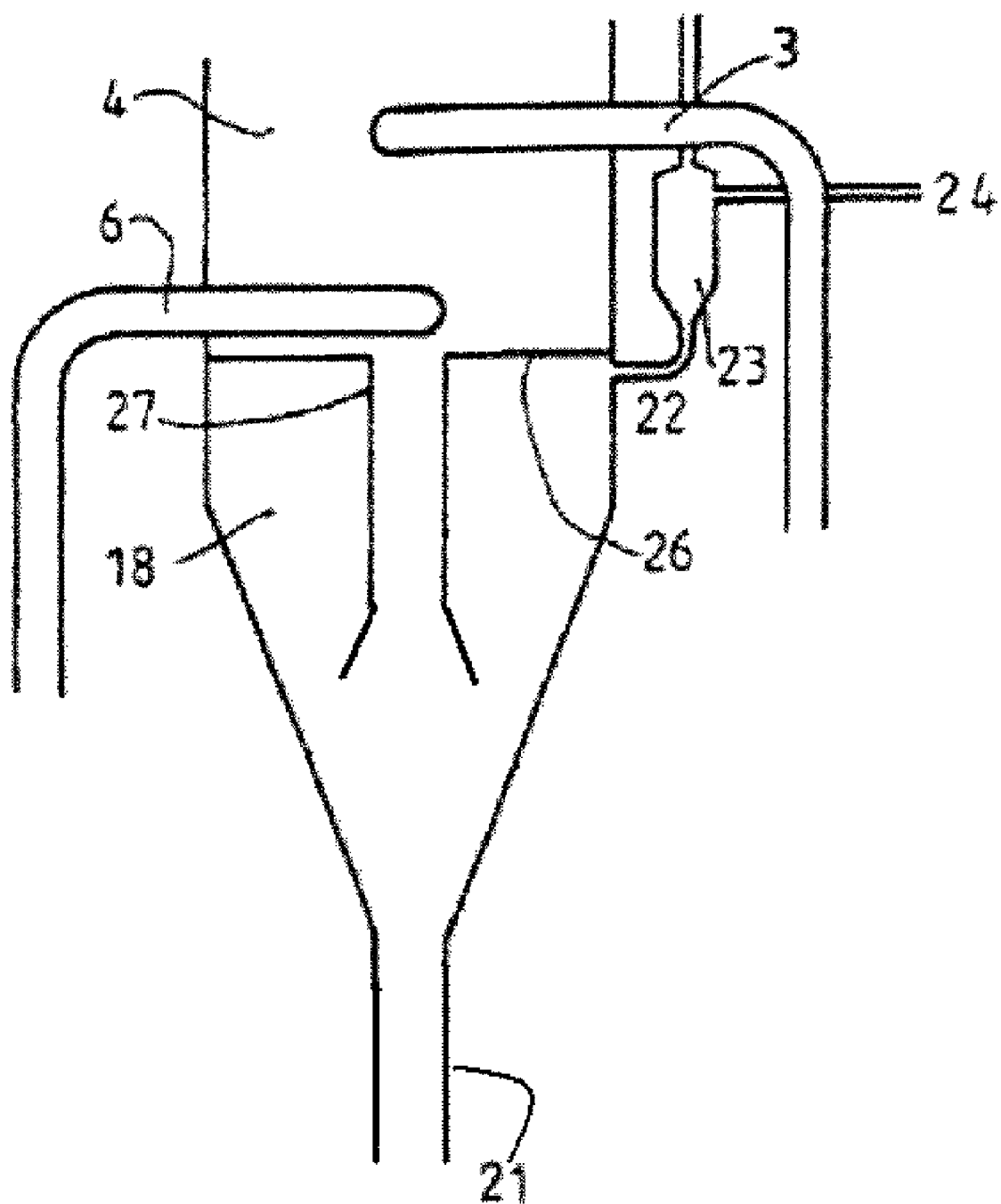
FIG. 2 is an illustration of a specific form of a decantation.

FIG. 2 illustrates in more detail a specific form of decantation coming within the scope of the invention. To prevent, on the one hand, the excessively rapid movements of the mass of catalyst and of hydrogenate from being propagated in the decanter (18) and, on the other hand, the hydrogen from entering the latter, separation between the two regions (gas/liquid separation section and liquid/solid separation section) is necessary. However, it must not in any way be the cause of deposition of catalyst. Such a result is obtained by virtue of the installation of a partition (26) between the separator (4) and the decanter (18), the circulation between the gas/liquid separator and the decanter being provided by a pipeline (27) with a diameter calculated in order to significantly reduce the velocity of the liquid (for example to a value of less than 0.5 meter/second).

This pipeline (27) is extended inside the decanter by a pipe with a diameter greater than or equal to that of the pipeline (27).

The use of the device or installation described above for carrying out the process for the hydrogenation of adiponitrile to give hexamethylenediamine makes it possible to obtain good dispersion of the hydrogen in the liquid reaction mixture. This dispersion is stable and homogeneous throughout the U-shaped pipe or pipes.

This apparatus makes it possible, as was said above, to continuously separate, without significant deactivation of the catalyst, the hydrogenate to be withdrawn from the said catalyst to be recycled, making it possible to easily withdraw a portion of catalyst intended to be regenerated.

According to the invention, a portion of the catalyst slurry recycled via the line (21) is withdrawn via a valve (32).

The stream of catalyst slurry thus separated is fed to an installation for washing with water (33), represented diagrammatically. This washing installation can comprise stirred washers or one or more washing columns, in particular, for continuous operation, a countercurrent column.

The catalyst, after having been washed according to the conditions described above, is fed to a basic treatment installation (34). This installation can comprise one or more stirred reactors. The treatment of a strong base can be carried out batchwise or continuously.

After basic treatment, the regenerated catalyst is fed to a further washing installation (35) similar to the installation (33).

The regenerated and washed catalyst is, in the example illustrated, mixed with the stream of fresh catalyst fed to the reactor part (9) via the pipe (30).

In another embodiment, the regenerated catalyst is fed directly to the reactor (9).

Details and advantages of the invention will be illustrated in the examples given below purely by way of indication.

EXAMPLE 1

Adiponitrile is continuously hydrogenated to give hexamethylenediamine at a temperature of 82° C. and a pressure of 23 bar in an installation represented in FIG. 1. The reaction medium comprises adiponitrile fed via the pipe (13), hydrogen fed via the pipe (17), potassium hydroxide, hexamethylenediamine, water and a catalyst comprising Raney nickel. A portion of spent catalyst corresponding to the amount of fresh catalyst fed is removed.

The flow rates of adiponitrile and of fresh catalyst are determined in order to have production of hexamethylenediamine with a selectivity of greater than or equal to 98.5%.

According to the invention, a portion of the catalyst slurry recycled via the pipeline (21) is separated via the valve (32) and fed to a regeneration process. The flow rate by weight of catalyst thus separated is represented by the value R.

The catalyst slurry is, in a first stage, washed with water at a temperature of 40° C. Several successive washing operations are carried out. The concentration of hexamethylenediamine, determined by gas chromatographic assaying, in the final aqueous washing liquor is 3000 ppm.

The washed catalyst is introduced, in a second stage, into a stirred reactor with a 20% by weight sodium hydroxide solution. The mixture is maintained at the boiling point of the medium for 3 hours.

The treated catalyst is subsequently, in a first stage, washed with water at 80° C. Several successive washing operations are carried out. The final aqueous washing liquor comprises 0.03% by weight of sodium hydroxide.

The catalyst thus obtained exhibits a catalytic activity equal to 60% of the catalytic activity of the fresh catalyst.

The regenerated catalyst, with a flow rate by weight R, is mixed with the fresh catalyst, exhibiting a flow rate by weight N, so as to maintain a regenerated catalyst ratio $R/(R+N)$ equal to 0.8.

Under these conditions, for optimum functioning of the reactor, the consumption of fresh catalyst per tonne of HMD produced is 0.50 kg.

COMPARATIVE EXAMPLE

Example 1 is repeated, except that all the separated catalyst is recycled to the reactor via the pipeline (21).

As in Example 1, the flow rates of adiponitrile and of fresh catalyst are determined in order to have production of hexamethylenediamine with a selectivity of greater than or equal to 98.5%.

Under these conditions, for optimal functioning of the reactor, the consumption of fresh catalyst per tonne of HMD produced is 1.35 kg.

The invention claimed is:

1. A continuous process for the preparation of at least one amino compound containing at least one amine functional group, comprising:
   (a) continuously hydrogenating at least one compound containing at least one nitrile functional group in an alcohol-free reaction medium which comprises particulates of a Raney metal catalyst, an inorganic base and water,
   (b) separating a portion of the catalyst from the medium,
   (c) regenerating a portion of the catalyst separated from the medium by:
      i) washing the catalyst with water to remove organic compounds,
      ii) treating the washed catalyst with a strong base and
      iii) washing the catalyst treated with the strong base with an aqueous alkali metal hydroxide solution and/or water, and
   (d) returning regenerated catalyst to the reaction medium along with a portion of fresh catalyst.

2. A continuous process for the preparation of at least one compound containing at least one amine functional group by hydrogenation of at least one compound containing at least one nitrile functional group, said process comprising:

feeding (1) a gas stream comprising hydrogen and (2) at least one compound containing at least one nitrile functional group into a plug-flow reactor in which a reaction medium is circulating, the reaction medium comprising suspended particles of catalyst based on Raney metal, an inorganic base and water;

separating, at the outlet of the plug-flow reactor, a portion of the catalyst from a portion of the reaction medium comprising the at least one compound containing at least one amine functional group, and recycling the remaining portion of the reaction medium separated from the catalyst to the plug-flow reactor;

recycling the separated catalyst to the plug-flow reactor; and feeding a stream of fresh catalyst to the plug-flow reactor, wherein a portion of the separated catalyst is subjected to a regeneration process comprising a first stage of washing with water to remove organic compounds and providing a final aqueous washing liquor, a second stage of treatment with a strong base and a third stage of washing with an aqueous alkali metal hydroxide solution and/or water and providing a final aqueous washing liquor.

3. The continuous process as defined by claim 2, wherein the regenerated catalyst is introduced to the plug-flow reactor at a mass flow rate R (in weight of catalyst per unit time) and the fresh catalyst is introduced to the plug-flow reactor at a mass flow rate N (in weight of catalyst per unit time) and the mass flow rate R of recycled regenerated catalyst and the mass flow rate N for feeding with fresh catalyst satisfies the following equation I:

$$0.60 \le \frac{R}{R+N} \le 0.95. \quad (I)$$

4. The continuous process as defined by claim 3, wherein the mass flow rate R of recycled regenerated catalyst and the mass flow rate N for feeding with fresh catalyst satisfies the following equation II:

$$0.70 \le \frac{R}{R+N} \le 0.90. \quad (II)$$

5. The continuous process as defined by claim 2, wherein the first stage of washing with water is carried out with water at a temperature ranging from 10° C. to 50° C.

6. The continuous process as defined by claim 2, wherein the final aqueous washing liquor in the first stage has a concentration of organic compounds of less than or equal to 1% by weight.

7. The continuous process as defined by claim 2, wherein the treatment with a strong base is carried out with an aqueous solution comprising an alkali metal hydroxide.

8. The continuous process as defined by claim 7, wherein the alkali metal hydroxide comprises sodium hydroxide.

9. The continuous process as defined by claim 7, wherein the concentration of alkali metal hydroxide in said aqueous solution ranges from 10% to 25% by weight.

10. The continuous process as defined by claim 7, wherein the basic treatment is carried out at a temperature of greater than 80° C.

11. The continuous process as defined by claim 2, wherein the washing with water in the third stage is carried out with water and/or an aqueous alkali metal hydroxide solution having a minimum concentration of alkali metal hydroxide of 0.012% by weight at a temperature ranging from 40° C. to 90° C.

12. The continuous process as defined by claim 2, wherein the final aqueous washing liquor in the third stage has a concentration of alkali metal hydroxide of greater than or equal to 0.012% by weight.

13. The continuous process as defined by claim 11, wherein the alkali metal hydroxide is sodium hydroxide.

14. The continuous process as defined by claim 2, wherein the regeneration process is carried out under air.

15. The continuous process as defined by claim 2, wherein the regeneration of the catalyst is carried out under an inert atmosphere or an atmosphere not comprising oxygen.

16. The continuous process as defined by claim 15, wherein the aqueous liquors used for the washing stages and the alkali metal hydroxide solution are deoxygenated.

17. The continuous process as defined by claim 2, wherein the regenerated catalyst has a catalytic activity corresponding to 35% to 80% of the catalytic activity of the fresh catalyst.

18. The continuous process as defined by claim 17, wherein the regenerated catalyst has a catalytic activity corresponding to 40% to 70% of the catalytic activity of the fresh catalyst.

19. The continuous process as defined by claim 2, wherein the at least one nitrile compound comprises adiponitrile and the at least one amine synthesized comprises hexamethylenediamine.

20. The continuous process as defined by claim 2, wherein the reaction medium comprises a solvent including the amine produced by the hydrogenation reaction.

21. The continuous process as defined by claim 2, comprising, at the plug-flow reactor outlet, a region for decantation of the catalyst particles, recycling the supernatant phase to the plug-flow reactor via a first external loop which comprises a withdrawal of the medium comprising the amine, and recycling the decanted phase to the plug-flow reactor via a second external loop.

22. The continuous process as defined by claim 2, wherein the catalyst is based on Raney nickel or Raney cobalt.

23. The continuous process as defined by claim 22, wherein the catalyst comprises a promoter selected from the elements belonging to Groups IIB and IVB to VIIB of the Periodic Table of the Elements and combinations thereof.

24. The continuous process as defined by claim 2, wherein the inorganic base is selected from the group consisting of LiOH, NaOH, KOH, RbOH, CsOH and mixtures thereof.

25. The continuous process as defined by claim 24, wherein the inorganic base is selected from the group consisting of KOH and NaOH and mixtures thereof.

26. The continuous process as defined by claim 24, wherein the amount of base in the reaction medium ranges from 0.1 mol of base per kg of catalyst to 2 mol of base per kg of catalyst.

27. The continuous process as defined by claim 2, wherein the reaction temperature ranges from 50° C. to 150° C. and the hydrogen pressure ranges from 0.1 MPa to 10 MPa.

* * * * *